United States Patent
Heim et al.

(10) Patent No.: US 11,369,747 B2
(45) Date of Patent: Jun. 28, 2022

(54) SYRINGE WITH OPTIMISED CENTRE OF GRAVITY

(71) Applicant: Laboratoires Vivacy, Paris (FR)

(72) Inventors: Ludovic Heim, Cran Gevrier (FR); Denis Gantin, Ayze (FR)

(73) Assignee: Laboratoires Vivacy, Paris (FR)

( * ) Notice: Subject to any disclaimer, the term of this patent is extended or adjusted under 35 U.S.C. 154(b) by 244 days.

(21) Appl. No.: 16/500,750

(22) PCT Filed: Mar. 29, 2018

(86) PCT No.: PCT/FR2018/050780
§ 371 (c)(1),
(2) Date: Oct. 3, 2019

(87) PCT Pub. No.: WO2018/185406
PCT Pub. Date: Oct. 11, 2018

(65) Prior Publication Data
US 2020/0078528 A1    Mar. 12, 2020

(30) Foreign Application Priority Data
Apr. 4, 2017  (FR) ...................... 1752876

(51) Int. Cl.
*A61M 5/315*   (2006.01)
*A61M 5/31*    (2006.01)

(52) U.S. Cl.
CPC ...... *A61M 5/31573* (2013.01); *A61M 5/3137* (2013.01); *A61M 5/31511* (2013.01)

(58) Field of Classification Search
CPC ............ A61M 5/31573; A61M 5/3137; A61M 5/31511; A61M 2205/586; A61K 31/728
See application file for complete search history.

(56) References Cited

U.S. PATENT DOCUMENTS

| 3,705,584 A | 12/1972 | Fript |
| 4,132,231 A | 1/1979 | Puccio |
| 2011/0288481 A1* | 11/2011 | Mudd .................... A61M 5/20 604/131 |

(Continued)

FOREIGN PATENT DOCUMENTS

| EP | 2574357 A1 | 4/2013 |
| WO | 2014033143 A1 | 3/2014 |

OTHER PUBLICATIONS

GLS Versaflex Data Sheet; Dec. 8, 2009; https://www.complex-global.com/upload_files/versaflex/OM3060-1.pdf (Year: 2009).*

(Continued)

*Primary Examiner* — Bradley J Osinski
(74) *Attorney, Agent, or Firm* — TraskBritt

(57) ABSTRACT

A syringe has a syringe body configured to receive a product for injection. Gripping wings are arranged at one end of the syringe body. A piston rod is mounted so as to be able to slide inside the syringe body. A stop is arranged at a first end of the piston rod and has an end-of-travel position inside the syringe body. A pusher is arranged at a second end of the piston rod. The pusher has a mass greater than or equal to a threshold value beyond which the syringe has a center of gravity situated outside the syringe body when the stop is in the end-of-travel position.

12 Claims, 4 Drawing Sheets

(56) References Cited

U.S. PATENT DOCUMENTS

| 2013/0218293 A1* | 8/2013 | Mita ...................... A61F 9/007 |
| | | 623/23.72 |
| 2014/0005668 A1* | 1/2014 | Rhee ..................... A61B 34/37 |
| | | 606/45 |
| 2014/0039456 A1 | 2/2014 | Lerner |
| 2015/0024335 A1* | 1/2015 | Sabourin ............. A61C 1/0015 |
| | | 433/27 |
| 2018/0133400 A1* | 5/2018 | Almoumen ......... A61M 5/3137 |
| 2018/0318519 A1* | 11/2018 | Lee ......................... A61M 5/32 |

OTHER PUBLICATIONS

European Communication pursuant to Article 94(3) EPC for European Application No. 18718599, dated Mar. 1, 2021, 9 pages (w/English translation).

International Search Report and International Written Opinion for International Application PCT/FR2018/050780, dated Jun. 19, 2018, 18 pages (including English translation).

* cited by examiner

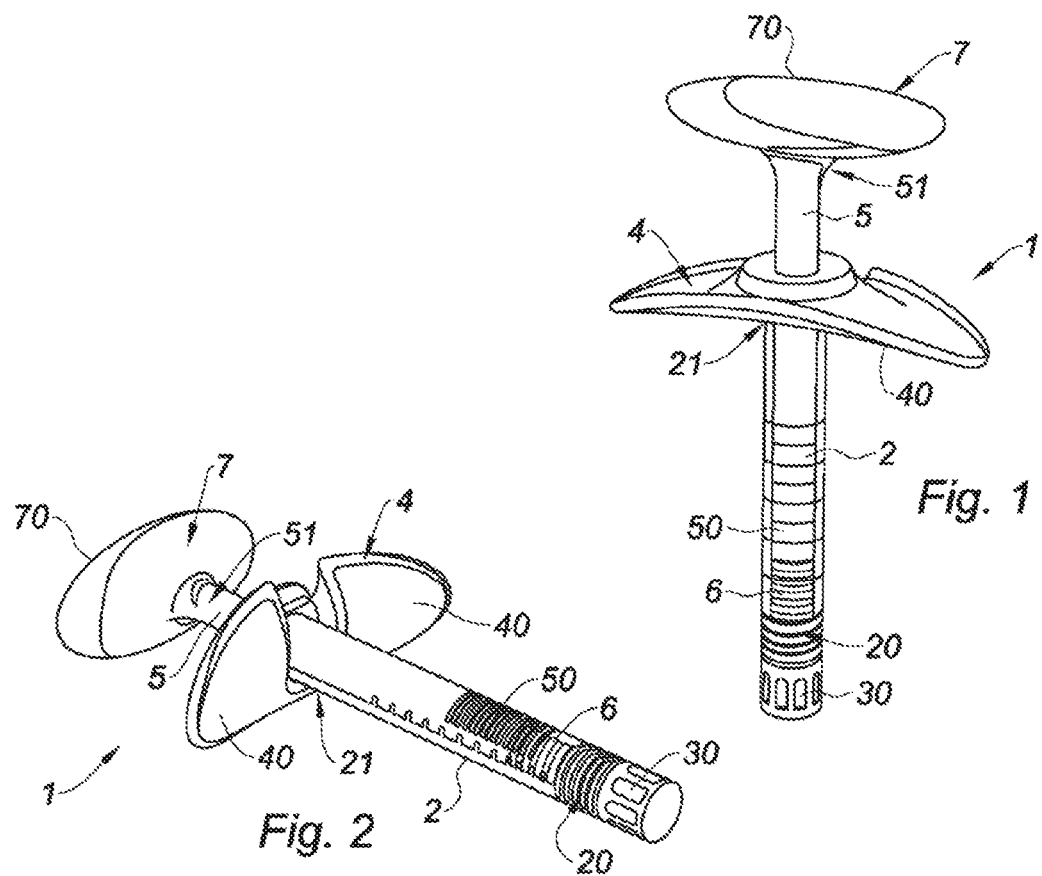
Fig. 1
Fig. 2
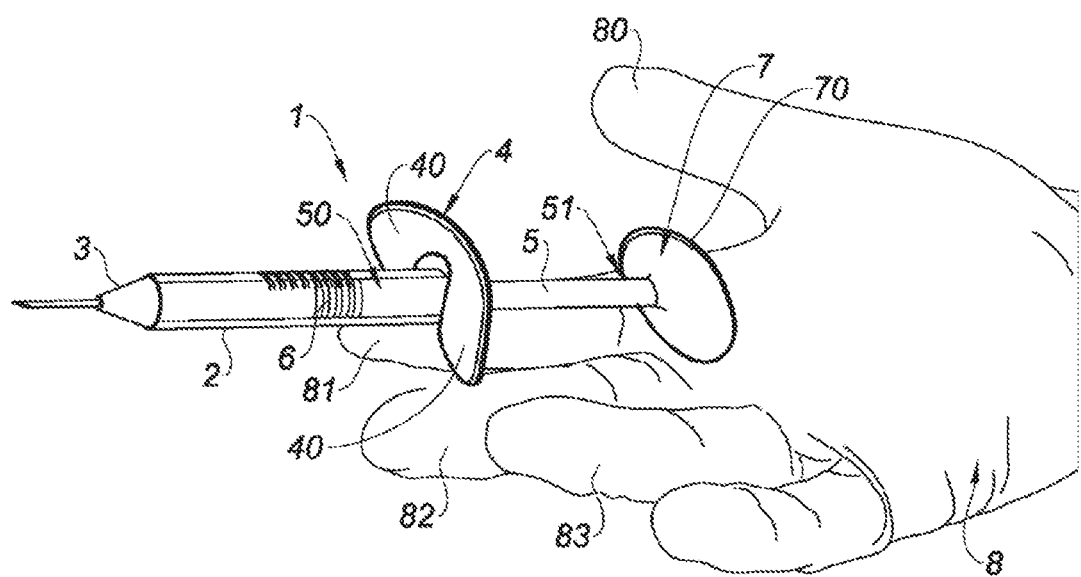
Fig. 3

SYRINGE WITH OPTIMISED CENTRE OF GRAVITY

CROSS-REFERENCE TO RELATED APPLICATIONS

This application is a national phase entry under 35 U.S.C. § 371 of International Patent Application PCT/FR2018/050780, filed Mar. 29, 2018, designating the United States of America and published in French as International Patent Publication WO 2018/185406 A1 on Oct. 11, 2018, which claims the benefit under Article 8 of the Patent Cooperation Treaty to French Patent Application Serial No. 1752876, filed Apr. 4, 2017.

TECHNICAL FIELD

This disclosure relates to the technical field of syringes.

This disclosure has an application, in particular, in the injection of viscoelastic gels based on hyaluronic acid, in the field of anti-aging procedures and medical esthetics.

BACKGROUND

A syringe known from the prior art has:
- a syringe body, intended to receive a product for injection, the syringe body having a first end, intended to be equipped with a needle holder, and a second, opposite end;
- gripping wings, arranged at the second end of the syringe body;
- a piston rod, mounted so as to be able to slide inside the syringe body, the piston rod having a first end and a second, opposite end;
- a stop, arranged at the first end of the piston rod, and having an end-of-travel position inside the syringe body; and
- a pusher, arranged at the second end of the piston rod.

Such a syringe from the prior art is not entirely satisfactory when the product for injection requires considerable pressure to be applied to the pusher. This is especially the case when the product for injection is a viscoelastic gel based on hyaluronic acid, where it is generally necessary to apply a force of over 100 N. The physician is then likely to experience some degree of discomfort, or even pain, caused by repeated use of such a syringe from the prior art. The term "physician" will be used below, it being understood that the term designates any user of the syringe.

In addition, the product can be injected into a patient's wrinkles, more particularly under the eyes. Such an injection requires excellent stability of the syringe in order to achieve the desired precision (of the order of ±1 mm) and in order to reach the patient's wrinkles effectively and safely.

BRIEF SUMMARY

This disclosure aims to overcome all or some of the aforementioned disadvantages. To this end, the subject of the present disclosure is a syringe having:
- a syringe body, intended to receive a product for injection, the syringe body having a first end, intended to be equipped with a needle holder, and a second, opposite end;
- gripping wings, arranged at the second end of the syringe body;
- a piston rod, mounted so as to be able to slide inside the syringe body, the piston rod having a first end and a second, opposite end;
- a stop, arranged at the first end of the piston rod, and having an end-of-travel position inside the syringe body; and
- a pusher, arranged at the second end of the piston rod;

the syringe being characterized in that the pusher has a mass greater than or equal to a threshold value beyond which the syringe has a center of gravity situated outside the syringe body when the stop is in the end-of-travel position.

Thus, such a syringe according to the present disclosure has excellent stability by virtue of such positioning of the center of gravity, which permits great precision during the injection. Indeed, the center of gravity of the syringe according to the present disclosure is offset in relation to the prior art, being closer to the hand of the physician exerting pressure on the pusher. This also makes it possible to improve the comfort felt by the physician upon repeated use.

In addition, such a syringe according to the present disclosure promotes the reproducibility of the positioning of the syringe in the hand of the physician, which contributes to improving the precision during the injection. Indeed, such positioning of the center of gravity facilitates the tilting of the syringe toward the palm of the physician's hand. The physician's fingers on which the gripping wings rest form a bearing surface, which is a base for supporting the syringe. The line of action of the weight of the syringe must be outside the support base in order to ensure that the syringe is able to tilt toward the palm of the physician's hand. The fact that the center of gravity of the syringe is outside the syringe body when the stop is in the end-of-travel position makes it possible to obtain a center of gravity away from the gripping wings, hence a center of gravity away from the support base, which therefore subsequently facilitates the tilting of the syringe, because the line of action of the weight of the syringe can be located more rapidly outside the support base.

The syringe according to the present disclosure can have one or more of the following features.

According to one feature of the present disclosure, the center of gravity is situated inside the piston rod, between the gripping wings and the pusher, when the stop is in the end-of-travel position.

Thus, one advantage afforded is that of achieving a compromise between stability and maneuverability of the syringe, which may be useful for certain uses.

According to one feature of the present disclosure, the center of gravity is situated in proximity to the second end of the piston rod when the stop is in the end-of-travel position.

Thus, one advantage afforded is that of bringing the center of gravity of the syringe closer to the physician's hand in order to increase the stability of the syringe when the pressure exerted on the pusher is considerable.

In addition, such positioning of the center of gravity promotes the tilting of the syringe toward the palm of the physician's hand in order to obtain excellent reproducibility of the positioning of the syringe in the physician's hand.

According to one feature of the present disclosure, the syringe body, the gripping wings, the piston rod and the stop have a total mass, and the threshold value of the mass of the pusher is determined according to the total mass.

Thus, one advantage afforded is that of being able to position the center of gravity of the syringe while taking into account different possible configurations of the syringe (geometry, type of material used, etc.).

According to one feature of the present disclosure, the threshold value of the mass of the pusher is 4 grams.

Thus, it has been found that this threshold value makes it possible to obtain a center of gravity situated outside the syringe body when the stop is in the end-of-travel position, and this applies for conventional syringe designs.

According to one feature of the present disclosure, the pusher has a gripping surface, preferably of elliptical shape, having a surface area of between 800 mm² and 900 mm².

Thus, one advantage afforded is that of enlarging the gripping surface of the pusher by comparison with the prior art (by the order of 80% compared to conventional syringe designs), which makes it possible, in particular, to actuate the pusher with the palm of the hand (not simply with the thumb) without adversely affecting the stability of the syringe.

The gripping surface of the pusher is preferably elliptical in order to avoid the presence of sharp edges that could injure the physician.

In addition, an enlarged gripping surface of the pusher confers greater freedom as regards the angles of injection.

According to one feature of the present disclosure, the gripping wings have a gripping surface that has a surface area of between 700 mm² and 800 mm², preferably of between 700 mm² and 750 mm².

Thus, one advantage afforded is that of enlarging the gripping surface of the gripping wings by comparison with the prior art (by the order of 90% compared to conventional syringe designs). This results in an improved stability of the syringe by enlarging the surface of contact with the physician's fingers. Moreover, such an enlargement of the gripping surface (and therefore of its mass) is compensated by a suitable mass of the pusher in order to maintain a center of gravity situated outside the syringe body when the stop is in the end-of-travel position.

According to one feature of the present disclosure, the gripping wings have a concave gripping surface oriented toward the first end of the syringe body.

Thus, one advantage afforded by the concavity of the gripping surface is that of being able to avoid the physician's fingers slipping sideways on the gripping surface and of thus making the injection maneuver safer.

According to one feature of the present disclosure, the gripping wings extend along a longitudinal axis and have a transverse profile forming a convex surface.

Thus, one advantage afforded by such a transverse profile is that of facilitating the tilting of the syringe toward the palm of the physician's hand, by virtue of the convexity of the surface.

According to one feature of the present disclosure, the syringe body, the gripping wings, the piston rod and the pusher are made at least partially of a first plastics material, preferably polycarbonate; the pusher has a gripping surface made at least partially of a second plastics material different than the first plastics material and having a hardness of between 30 Shore A and 70 Shore A, preferably of between 50 Shore A and 70 Shore A; the gripping wings have a gripping surface made at least partially of the second plastics material.

Thus, such a second plastics material is sufficiently soft to obtain an excellent hold. Moreover, the use of two distinct plastics materials can give the syringe, according to the present disclosure, an attractive appearance.

BRIEF DESCRIPTION OF THE DRAWINGS

Other features and advantages will become clear from the following detailed description of various embodiments of the present disclosure, the description containing examples and references to the attached drawings.

FIG. 1 is a schematic perspective view of a syringe according to the present disclosure, in a vertical position, in the absence of a needle holder.

FIG. 2 is a schematic view similar to FIG. 1, illustrating the syringe in a horizontal position.

FIG. 3 is a schematic perspective view of a syringe according to the present disclosure, in a horizontal position in a physician's hand, and equipped with a needle holder.

DETAILED DESCRIPTION

Figure 4:
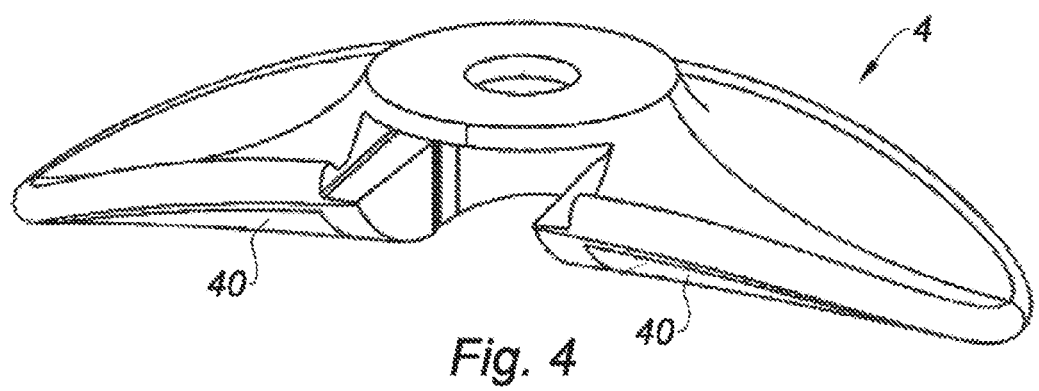
FIG. 4 is a schematic perspective view of gripping wings with which a syringe, according to the present disclosure, is equipped.
Figure 5:
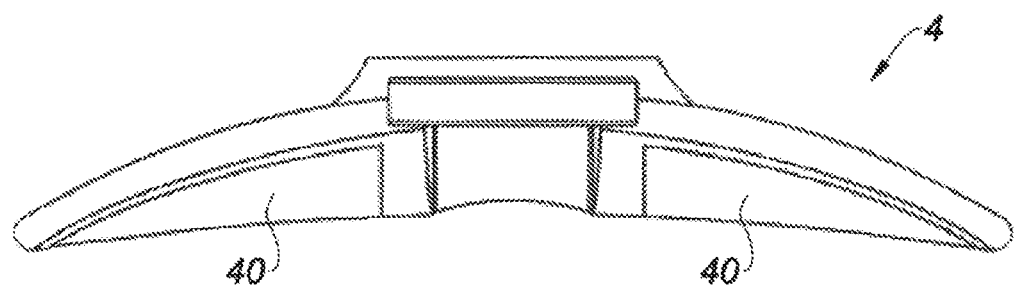
FIG. 5 is a schematic longitudinal sectional view of the gripping wings illustrated in FIG. 4; "longitudinal" is understood as a direction along the longitudinal axis of the gripping wings.

Those elements that are identical or that perform the same function will bear the same references in the various embodiments, for the sake of simplicity.

A subject of the present disclosure is a syringe 1 having:
- a syringe body 2, intended to receive a product for injection, the syringe body 2 having a first end 20, intended to be equipped with a needle holder 3, and an opposite, second end 21;
- gripping wings 4, arranged at the second end 21 of the syringe body 2;
- a piston rod 5, mounted so as to be able to slide inside the syringe body 2, the piston rod 5 having a first end 50 and an opposite, second end 51;
- a stop 6, arranged at the first end 50 of the piston rod 5, and having an end-of-travel position inside the syringe body 2; and
- a pusher 7, arranged at the second end 51 of the piston rod 5;

the syringe being characterized in that the pusher 7 has a mass greater than or equal to a threshold value beyond which the syringe 1 has a center of gravity situated outside the syringe body 2 when the stop 6 is in the end-of-travel position.

Syringe Body

The syringe body 2 is preferably cylindrical. The product for injection is preferably a viscoelastic gel based on hyaluronic acid.

The first and second ends 20, 21 of the syringe body 2 are open. The first end 20 of the syringe body 2 is open in order to receive a needle holder 3. In the absence of a needle holder 3, as illustrated in FIGS. 1 and 2, the first end 20 of the syringe body 2 is preferably closed by a cap 30. The second end 21 of the syringe body 2 is open in order to receive the piston rod 5.

Advantageously, the syringe body 2 is made of a first plastics material. The first plastics material is preferably polycarbonate.

Piston Rod and Stop

Advantageously, the piston rod 5 is made of the first plastics material.

The stop 6 forms a piston head. When the stop 6 is in the end-of-travel position, the piston rod 5 advantageously protrudes from the syringe body 2 by a distance of between 20 mm and 30 mm.

Pusher

The pusher 7 advantageously has a mass greater than or equal to a threshold value beyond which the center of gravity of the syringe 1 is situated inside the piston rod 5, between the gripping wings 4 and the pusher 7, when the stop 6 is in the end-of-travel position.

The pusher 7 advantageously has a mass greater than or equal to a threshold value beyond which the center of gravity of the syringe 1 is situated in proximity to the second end 51 of the piston rod 5 when the stop 6 is in the end-of travel position.

The syringe body 2, the gripping wings 4, the piston rod 5 and the stop 6 have a total mass. The threshold value of the mass of the pusher 7 is determined according to the total mass such that the syringe 1 has a center of gravity situated outside the syringe body 2 when the stop 6 is in the end-of-travel position.

The threshold value of the mass of the pusher 7 is advantageously 4 grams. The mass of the pusher 7 is advantageously less than or equal to 10 grams, so as not to make the syringe 1 needlessly heavy. The mass of the pusher 7 is advantageously between 4 grams and 5 grams.

The pusher 7 has a gripping surface 70, preferably of elliptical shape, advantageously having a surface area of between 800 mm$^2$ and 900 mm$^2$.

Advantageously, the pusher 7 is made at least partially of the first plastics material. Advantageously, the pusher 7 has a gripping surface 70 made at least partially of a second plastics material different than the first plastics material. The second plastics material advantageously has a hardness of between 30 Shore A and 70 Shore A, preferably of between 50 Shore A and 70 Shore A. By way of non-limiting examples, the second plastics material can be a thermoplastic of the SEBS type, i.e., polystyrene-b-poly(ethylene-butylene)-b-polystyrene, or silicone.

Figure 10:
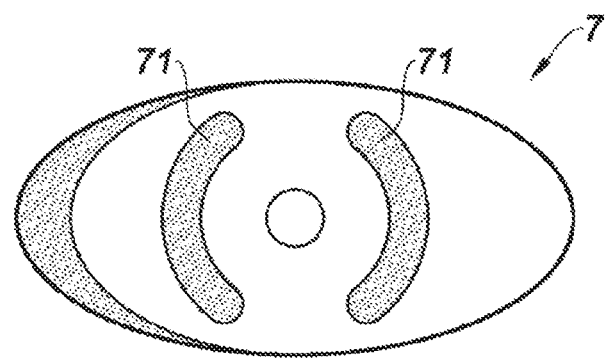
FIG. 10 is a schematic view of a pusher with which a syringe, according to the present disclosure, is equipped, illustrating the surface of the pusher oriented toward the gripping wings.
Figure 11:
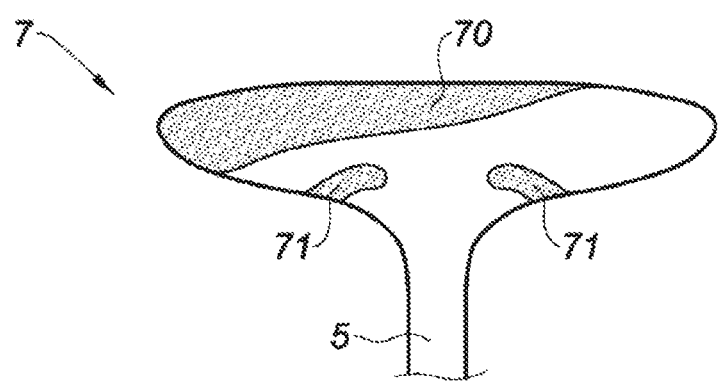
FIG. 11 is a schematic view of a profile of a pusher with which a syringe, according to the present disclosure, is equipped.

As is illustrated in FIGS. 10 and 11, the pusher 7 advantageously has at least one additional gripping surface 71, opposite the gripping surface 70. The one or more additional gripping surfaces 71 are advantageously made at least partially of the second plastics material. Such additional gripping surfaces 71 make it easier for the physician to draw back the product for injection.

Gripping Wings

The gripping wings 4 have a gripping surface 40 that advantageously has a surface area of between 700 mm$^2$ and 800 mm$^2$, preferably of between 700 mm$^2$ and 750 mm$^2$. The gripping wings 4 form lateral parts protruding from the syringe body 2 and in the form of a wing. The gripping wings 4 are advantageously in one piece.

The gripping wings 4 advantageously have a concave gripping surface 40 oriented toward the first end 20 of the syringe body 2.

Figure 6:
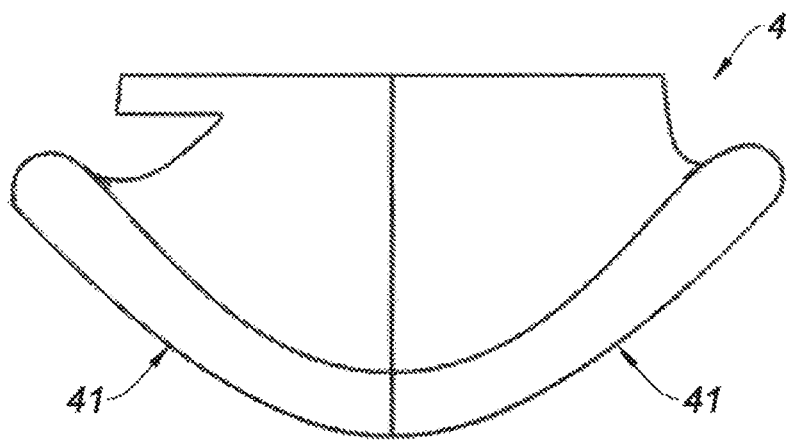
FIG. 6 is a schematic transverse sectional view of the gripping wings illustrated in FIG. 4; "transverse" is understood as a direction perpendicular to the longitudinal axis of the gripping wings.

The gripping wings 4 extend along a longitudinal axis and advantageously have a transverse profile forming a convex surface 41 (clearly visible in FIG. 6).

Advantageously, the gripping wings 4 are made at least partially of the first plastics material. Advantageously, the gripping wings 4 have a gripping surface 40 that is made at least partially of the second plastics material.

Manipulation of the Syringe

Figure 7:
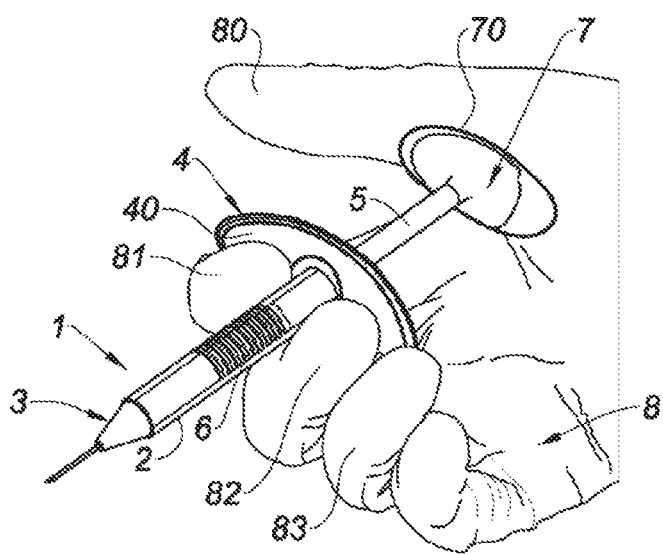
FIGS. 7 to 9 are schematic perspective views of a syringe, according to the present disclosure, in a physician's hand, illustrating different positions of the fingers permitting the injection.
Figure 8:
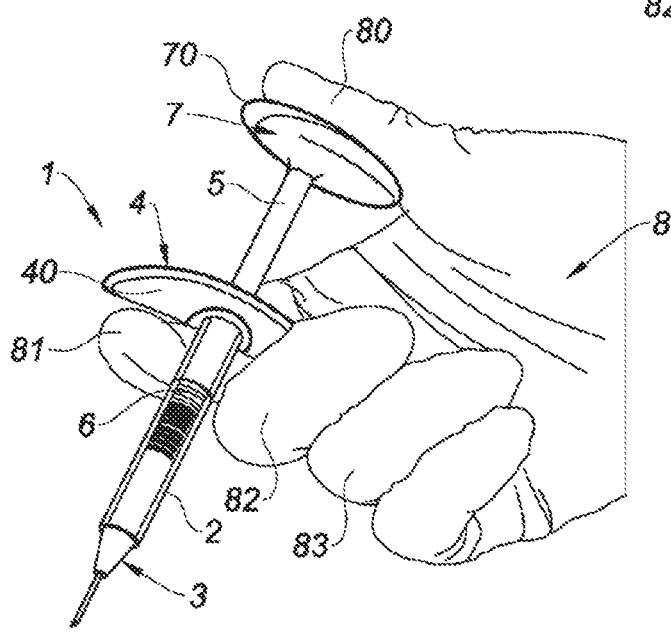
Figure 9:
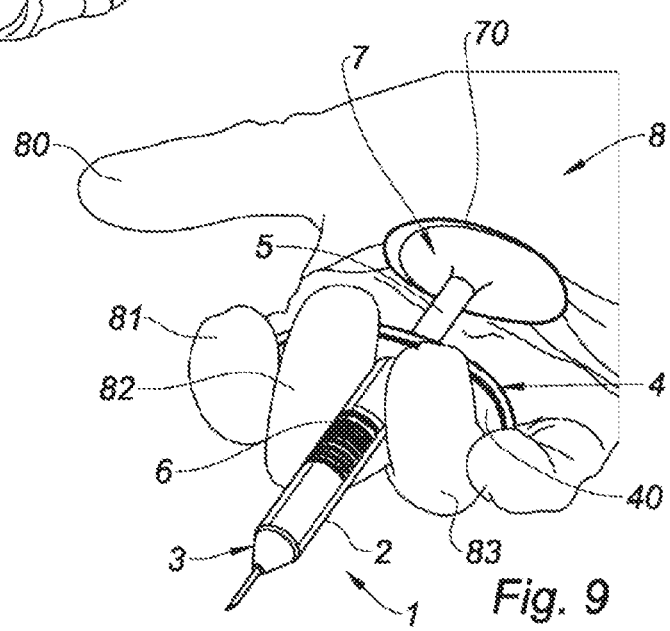

As is illustrated in FIGS. 7 to 9, different manipulations of the syringe 1 according to the present disclosure, are possible, this being permitted, in particular, by the substantial surface areas of the gripping surfaces 40, 70 of the gripping wings 4 and of the pusher 7, and also by the position of the center of gravity of the syringe 1. These different manipulations of the syringe 1 are reflected by the different positions of the syringe 1 in the hand 8 of the physician.

In the position illustrated in FIG. 7, the syringe body 2 is held between the index finger 81 and the middle finger 82 of the physician, said fingers resting on the gripping wings 4, while the pusher 7 is actuated by the base of the thumb 80.

In the position illustrated in FIG. 8, the syringe body 2 is held between the index finger 81 and the middle finger 82 of the physician, said fingers resting on the gripping wings 4, while the pusher 7 is actuated by the pad of the thumb 80.

In the position illustrated in FIG. 9, the syringe body 2 is held between the middle finger 82 and the ring finger 83 of the physician, said fingers resting on the gripping wings 4, while the pusher 7 is actuated by the palm of the hand 8.

The present disclosure is not limited to the embodiments shown. A person skilled in the art is able to consider the technically effective combinations thereof and to replace them with equivalents.

The invention claimed is:

1. A syringe, comprising:
    a syringe body configured to receive a product for injection, the syringe body having a first end, configured to be equipped with a needle holder, and a second end opposite the first end;
    gripping wings at the second end of the syringe body;
    a piston rod mounted so as to be able to slide inside the syringe body, the piston rod having a first end and a second end opposite the first end of the piston rod;
    a stop at the first end of the piston rod and having an end-of-travel position inside the syringe body, the end-of-travel position being a position after injection of the product; and
    a manual pusher at the second end of the piston rod, the manual pusher being designed to be subjected to a manually exerted pressure so as to inject the product,
    the piston rod having a free external surface, uncovered from the second end of the syringe body to the manual pusher,
    the syringe body, the gripping wings, the piston rod, and the stop together having a total mass,
    the manual pusher having a mass greater than or equal to a threshold value, determined according to the total mass, beyond which the syringe has a center of gravity situated outside the syringe body, inside the piston rod, between the gripping wings and the manual pusher, when the stop is in the end-of-travel position.

2. The syringe of claim 1, wherein the center of gravity is situated in proximity to the second end of the piston rod when the stop is in the end-of-travel position.

3. The syringe of claim 1, wherein the threshold value of the mass of the pusher is 4 grams.

4. The syringe of claim 1, wherein the pusher has a gripping surface with a surface area of between 800 mm² and 900 mm².

5. The syringe of claim 4, wherein the gripping surface of the manual pusher has an elliptical shape.

6. The syringe of claim 1, wherein the gripping wings have a gripping surface with a surface area of between 700 mm² and 800 mm².

7. The syringe of claim 1, wherein the gripping wings have a concave gripping surface oriented toward the first end of the syringe body.

8. The syringe of claim 1, wherein the gripping wings extend along a longitudinal axis and have a transverse profile forming a convex surface.

9. The syringe of claim 1, wherein:
   the syringe body, the gripping wings, the piston rod, and the manual pusher are made at least partially of a first plastics material;
   the manual pusher has a gripping surface at least partially made of a second plastics material different than the first plastics material and having a hardness of between 30 Shore A and 70 Shore A; and
   the gripping wings have another gripping surface made at least partially of the second plastics material.

10. The syringe of claim 9, wherein the first plastics material is polycarbonate.

11. The syringe of claim 9, wherein the hardness of the second plastics material is between 50 Shore A and 70 Shore A.

12. The syringe of claim 1, wherein the gripping wings have a gripping surface with a surface area of between 700 mm² and 750 mm².

* * * * *